United States Patent [19]

Chapleo et al.

[11] Patent Number: 5,385,919
[45] Date of Patent: Jan. 31, 1995

[54] IMIDAZOLINYL INDOLE DERIVATIVES USEFUL IN THE TREATMENT OF DIABETES

[75] Inventors: Christopher B. Chapleo, Swanland; Gay P. Fagan, Brandesburton, both of United Kingdom

[73] Assignee: Reckitt & Colman Products Limited, London, England

[21] Appl. No.: 39,232

[22] PCT Filed: Oct. 10, 1991

[86] PCT No.: PCT/GB91/01756

§ 371 Date: May 5, 1993

§ 102(e) Date: May 5, 1993

[87] PCT Pub. No.: WO92/06972

PCT Pub. Date: Apr. 30, 1992

[30] Foreign Application Priority Data

Oct. 20, 1990 [GB] United Kingdom ............... 9022858

[51] Int. Cl.[6] ............... A61K 31/415; A61K 31/47; C07D 401/04; C07D 403/04
[52] U.S. Cl. .................. 514/339; 514/397; 514/402; 546/273; 546/278; 548/312.1
[58] Field of Search .............. 548/312.1; 514/397, 514/402, 339; 546/273, 278

[56] References Cited

U.S. PATENT DOCUMENTS

| 2,751,393 | 6/1956 | Schindler et al. | 548/312.1 |
|---|---|---|---|
| 4,328,345 | 5/1982 | Steinman et al. | 548/312.1 X |
| 4,659,731 | 4/1987 | Bigg et al. | 514/397 |
| 4,908,376 | 3/1990 | Huebner et al. | 514/402 |
| 4,912,125 | 3/1990 | Huebner et al. | 548/312.1 X |
| 4,987,146 | 1/1991 | Rohde et al. | 548/312.1 X |
| 5,017,584 | 5/1991 | Hlasta | 514/314 |

FOREIGN PATENT DOCUMENTS

| 0107618 | 5/1984 | European Pat. Off. | 548/312.1 |
|---|---|---|---|
| 0141686 | 5/1985 | European Pat. Off. | 548/312.1 |
| 0211698 | 2/1987 | European Pat. Off. | 548/312.1 |
| 0429257 | 5/1991 | European Pat. Off. | 548/312.1 |
| 2-188579 | 7/1990 | Japan | 548/312.1 |

OTHER PUBLICATIONS

Fagan et al., *Journal of Medicinal Chemistry*, 1988, 31, 944–948.
Hlasta et al., *Journal of Medicinal Chemistry*, 1987, 30, 1555–1562.

*Primary Examiner*—Floyd D. Higel
*Attorney, Agent, or Firm*—Bacon & Thomas

[57] ABSTRACT

The invention relates to compound of formula I:

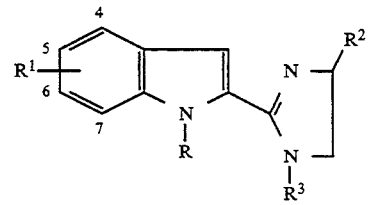

wherein $R^1$ is hydrogen or hydroxy; $R^2$ is hydrogen or methyl; $R^3$ is hydrogen or methyl; and R is 2-pyridyl, 3-pyridyl or $-C_6H_4-R^4$, where $R^4$ is hydrogen or hydroxy, or a non-toxic salt thereof, which are useful in the treatment of diabetes.

16 Claims, No Drawings

"5,385,919"
1

IMIDAZOLINYL INDOLE DERIVATIVES USEFUL IN THE TREATMENT OF DIABETES

This invention relates to indole derivatives, their non-toxic salts, processes for their preparation and pharmaceutical compositions of the derivatives or their salts for use in the treatment of diabetes.

Type 2 or maturity onset diabetes is characterised by raised plasma glucose levels in the fasting state and also by glucose intolerance following the ingestion of carbohydrate. Although postprandial elevations in plasma glucose are associated with deficient insulin secretion, plasma insulin levels appear to be in the normal range during fasting conditions. This latter observation is however misleading since when resting plasma insulin levels are related to the prevailing hyperglycaemia they are inappropriately low. Although the underlying cause of Type 2 diabetes is controversial there is now increasing evidence that the primary lesion is a defective insulin secretory process (Cerasi and Luft, Diabetes (1967) 16, 615; O'Rahilly et al, Lancet (1986), 360) which is exacerbated by a reduction in the efficacy of insulin (reduced insulin sensitivity). In normal subjects insulin regulates hepatic glucose production and defects in either the release or efficacy of insulin lead to an increased glucose production by the liver. The hyperglycaemic state is further enhanced by peripheral insulin insensitivity (insulin resistance) which leads to a reduction in the uptake of glucose by muscles. Although it is now generally accepted that reduced beta-cell function is the primary defect in Type 2 diabetes, there is no doubt that insulin resistance is a feature of the disease, particularly in obese patients, and some workers maintain that insulin insensitivity is the more constant feature of the disease (Reaven, Diabetes Care, (1982) 7 (suppl 1), 17).

The most commonly used first line hypoglycaemic agents are the sulphonylureas. These compounds have a complex mechanism of action which, despite extensive studies, is not fully understood. In the short term sulphonylureas stimulate first phase insulin release i.e. release of preformed insulin from beta-cells. Although sulphonylureas are the most commonly used agents in Type 2 diabetes there are inherent limitations to their utility. An important drawback of these compounds is that their major effect is expressed at basal or low blood glucose concentrations with postprandial changes being unaffected.

U.S. Pat. No. 4,659,731 discloses and claims dihydroindoles of the formula

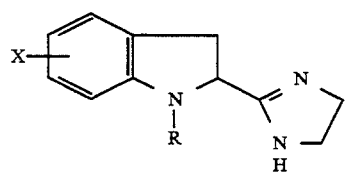

A in which

X is halogen, $(C_{1-4})$alkoxy, $(C_{1-4})$alkyl or allyloxy or, when

R is substituted or unsubstituted phenyl, X can also denote a hydrogen atom and

R is linear or branched $(C_{1-6})$alkyl, $(C_{3-6})$cycloalkyl, $(C_{1-4})$alkyl, $(C_{3-6})$alkenyl, benzyl which is unsubstituted or substituted by one or more halogen, methyl, methoxy and methylenedioxy substituents, or substituted phenyl of formula $-C_5H_4-Y$ in which Y is hydrogen, halogen, linear or branched $(C_{1-6})$alkyl or linear or branched $(C_{1-6})$alkoxy and salts thereof with pharmaceutically acceptable acid.

The compounds of formula A are said to be powerful $\alpha_2$-adrenoreceptor antagonists which can be used for the treatment of depression (either alone or in combination with a product which inhibits neuronal uptake mechanisms), the treatment of hypotension, the treatment of postoperative paralytic ileum, the treatment of asthma and obesity, the treatment of diabetes and the treatment of impotence.

The patent does not include test data for any specific compound. Included among the compounds described is a compound of formula B in which X is hydrogen and R is phenyl i.e. the compound:

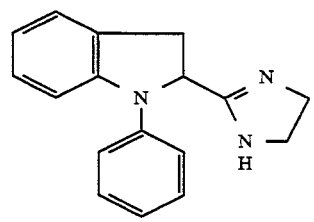

B isolated as the fumarate salt mp 212.5°–215° C.

In some of our earlier work, J. Med. Chem. 1988, 31, 944 there is described the synthesis and pharmacological evaluation, particularly as $\alpha_2$-adrenoreceptor antagonists, of a series of substituted 2-imidazolinylindolines of formula C

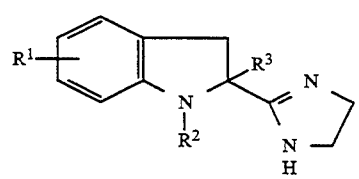

C

Included amongst the compounds of formula C prepared and tested was the earlier mentioned compound of formula 8 isolated as the hydrochloride salt mp 208°–209° C. This compound was found to be 0.5 times as potent as idazoxan as an $\alpha_2$-adrenoreceptor antagonist in the rat vas deferens test.

We have now extended our investigations to the analogous dehydro compounds and we have shown that whilst the direct analogue to the compound of formula 6 possesses only weak $\alpha_2$-adrenoreceptor antagonist activity (0.007 times as potent as idazoxan) most unexpectedly it possesses a significant level of antidiabetic activity.

According to the invention there is provided the use of 20 compounds of formula 1

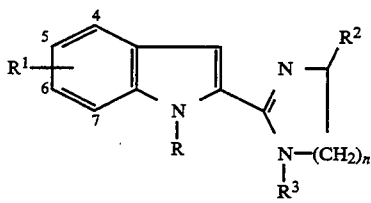

wherein
- $R^1$ is hydrogen or hydroxy,
- $R^2$ is hydrogen or methyl,
- $R^3$ is hydrogen or methyl,
- n is 1, 2 or 3, and
- R is n-alkyl $C_{1-3}$, n-alkenyl $C_{2-3}$, cyclopropylmethyl, 2-pyridyl, 3-pyridyl or —$C_6H_4$—$R^4$ (where $R^4$ is hydrogen or hydroxy);

or their non-toxic salts; for the manufacture of a medicament for the treatment of diabetes.

The compounds of formula 1 wherein $R^1$, $R^2$, $R^3$, n and R are as hereinbefore defined are novel; with the exception of the compound of formula 1 wherein $R^1$, $R^2$ and $R^3$ are hydrogen, n is 1 and R is methyl (J. Med. Chem. 1987, 30, 1555–1562 described as having weak $\alpha_2$-adrenoreceptor antagonist activity)

In a second aspect of the invention there are provided compounds of the formula 1 wherein
- $R^1$ is hydrogen or hydroxy,
- $R^2$ is hydrogen or methyl,
- $R^3$ is hydrogen or methyl,
- n is 1, 2 or 3, and
- R is n-alkyl $C_{1-3}$ especially n-propyl, n alkenyl $C_{2-3}$, cyclopropylmethyl, 2-pyridyl, 3-pyridyl or —$C_6H_4$—$R^4$ (where $R^4$ is hydrogen or hydroxy), provided that when $R^1$, $R^2$, and $R^3$ are hydrogen and n is 1 R is not methyl; and their non-toxic salts.

In a third aspect of the invention there are provided compounds of the formula 1

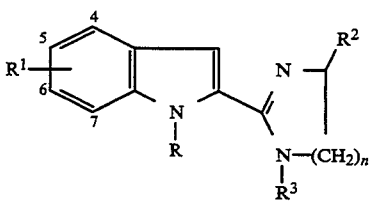

wherein
- $R^1$ is hydrogen or hydroxy,
- $R^2$ is hydrogen or methyl,
- $R^3$ is hydrogen or methyl,
- n is 1, 2 or 3, and
- R is 2-pyridyl, 3-pyridyl or —$C_6H_4$—$R^4$ (where $R^4$ is hydrogen or hydroxy);

and their non-toxic salts.

In a fourth aspect of the invention there are provided compounds of the formula 1 wherein
- $R^1$ is hydrogen or hydroxy in the 4 position,
- $R^2$ and $R^3$ are both hydrogen, or one of $R^2$ and $R^3$ is methyl and the other is hydrogen,
- n is 1, 2 or 3, and
- R is 2-pyridyl, 3-pyridyl or —$C_6H_4$—$R^4$ (where $R^4$ is hydrogen or 3-hydroxy); and their non-toxic salts.

The invention also includes pharmaceutical compositions comprising a compound of formula 1 or a non-toxic salt thereof, together with a pharmaceutically acceptable diluent or carrier.

Examples of non-toxic salts are those with inorganic acids such as hydrochloric acid, sulphuric or phosphonic acid; or organic acids such as acetic, propionic, malonic, succinic, fumaric, tartaric, citric or cinnamic acid.

We have found that the compounds of formula 1 exhibit antidiabetic activity in animal tests at doses which have little or no $\alpha_2$-adrenoreceptor antagonist properties at the level of the pancreas.

Compounds of formula 1 have primary action during hyperglycaemia in that they improve glucose tolerance without producing marked reduction in basal plasma glucose levels.

The invention further includes a method of treating diabetes in which an effective amount of a compound of formula 1 or a non-toxic salt thereof is administered to a patient requiring such treatment. Dosing frequency will range from once to three times a day with a dose of between 25 and 500 mg, preferably 50 to 250 mg per dose.

The compounds of formula 1 in which
- $R^1$ is hydrogen,
- $R^2$ is hydrogen or methyl,
- $R^3$ is hydrogen or methyl,
- n is 1, 2 or 3, and
- R is n-alkyl $C_{1-3}$, n-alkenyl $C_{2-3}$, cyclopropylmethyl, 2-pyridyl, 3-pyridyl or —$C_5H_4$—$R^4$ (where $R^4$ is hydrogen), may be prepared by reacting compounds of formula 2

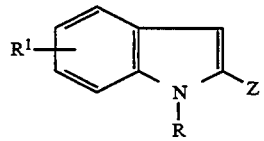

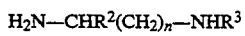

wherein $R^1$ and R are as herein defined and Z is $CO_2E$ (where E is methyl or ethyl); with trimethylaluminium and a compound of formula 3

$$H_2N—CHR^2(CH_2)_n—NHR^3 \qquad 3$$

wherein $R^2$, $R^3$ and n are as hereinbefore defined.

In an alternative process the compounds of formula 1 in which
- $R^1$ is hydrogen,
- $R^2$ is hydrogen or methyl,
- $R^3$ is hydrogen or methyl,
- n is 1, 2 or 3, and
- R is n-alkyl $C_{1-3}$, n-alkenyl $C_{2-3}$, cyclopropylmethyl, 2-pyridyl, 3-pyridyl or —$C_6H_4$—$R^4$ (where $R^4$ is hydrogen) may be prepared by reacting compounds of formula 2

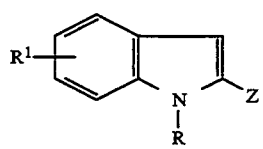

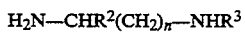

wherein $R^1$ and R are as hereinbefore defined and Z is CN; with a tosylate salt of a compound of formula 3

$$H_2N—CHR^2(CH_2)_n—NHR^3 \qquad 3$$

wherein $R^2$, $R^3$ and n are as hereinbefore defined; at a temperature of 150° to 200° C.

The compounds of formula 1 in which $R^1$ and/or $R^4$ is hydroxy may be prepared by reacting the analogous methoxy compounds of formula 1 in which $R^1$ and/or $R^4$ is methoxy with boron tribromide in dichloromethane. The said methoxy compounds may be prepared by either of the above general processes.

Compounds of formula 2 in which
Z is CN,
$R^1$ is hydrogen or methoxy, and
R is n-alkyl $C_{1-3}$, n-alkenyl $C_{2-3}$, cyclopropylmethyl, 2-pyridyl, 3-pyridyl or —$C_6H_4$—$R^4$ (where $R^4$ is hydrogen or methoxy)

may be prepared from the analogous compounds of formula 2, in which Z is $CO_2E$ (where E is methyl or ethyl), by successively hydrolysing to the corresponding acid (with, for example, sodium hydroxide in methanol), conversion to the corresponding acid chloride (by reaction with, for example, oxalyl chloride or thionyl chloride in dichloromethane at ambient temperature), conversion to the amide (by reaction with ammonia at 0°-5° C. in diethylether or dichloromethane), and finally conversion to the nitrile (by dehydration with thionyl chloride in dichloromethane and pyridine).

Compounds of formula 2 in which
$R^1$ is hydrogen or methoxy,
R is n-alkyl $C_{1-3}$, n-alkenyl $C_{2-3}$, cyclopropylmethyl, 2-pyridyl, 3-pyridyl or —$C_6H_4$—$R^4$ (where $R^4$ is hydrogen or methoxy), and
Z is $CO_2E$ (where E is methyl or ethyl) may be prepared from compounds of formula 4

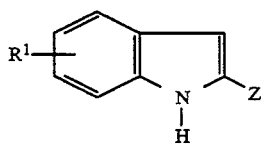

4 in which $R^1$ and Z are as hereinbefore defined, by standard alkylation or arylation processes as appropriate. For example where R is —$C_6H_5$ the compound of formula 4 is reacted with bromobenzene, under reflux conditions, in the presence of copper oxide and potassium carbonate, in pyridine, for 48 to 120 hours.

Compounds of formula 4 in which
$R^1$ is hydrogen or methoxy, and
Z is $CO_2E$ (where E is methyl or ethyl) may be prepared from the analogous compounds of formula 4 in which Z is —COOH, by esterification to either the methyl or ethyl ester by, for example, refluxing with methanol, or ethanol, and sulphuric acid.

The invention is illustrated by the following Examples. Melting points were determined on a Buchi apparatus in glass capillary tubes and are uncorrected. The various compounds and intermediates were examined by thin layer chromatography on silica gel plates (Merck, Kieselgel 60 $F_{254}$). NMR spectra were recorded on a Jeol FX90 instrument.

EXAMPLE 1

2-(2-Imidazolin-2-yl)-1-phenyl-1H-indole (a) Ethylenediamine (2 ml) was added dropwise to a cooled (0°-5° C.), stirred solution of trimethylaluminium (2M, 15 ml) in anhydrous toluene (150 ml) under an atmosphere of argon. The mixture was then allowed to warm to room temperature and a solution of ethyl 1-phenyl-1H-indole-2-carboxylate (8 g; Dolby L J, Lord P D, J Org Chem 1969, 34, 2988) in anhydrous toluene (100 ml) was added. The mixture was heated at reflux for 18 hours before water (100 ml) was added dropwise at room temperature with vigorous stirring. The inorganic salts were removed by filtration and the filtrate was extracted with dilute hydrochloric acid. The product was obtained by basifying the aqueous extract with sodium hydroxide solution and then extracting with dichloromethane.

The combined extracts were washed with water, dried ($Na_2SO_4$) and evaporated to give a white solid (3.8 g). Purification via column chromatography on silica eluting with methanolic ammonia (5%) in dichloromethane gave 2-(2-imidazolin-2-yl)-1-phenyl-1H-indole: yield 2.3 g (29%); mp 180°-182° C. Treatment of an ethanol solution of a sample of the free base with ethereal HCl gave the hydrochloride salt; mp 263.5°-265° C.

(b) A stirred mixture of 1-phenyl-1H-indole-2-carbonitrile (15 g) and ethylenediamine monotosylate (17.6 g) was heated at 200° C. for 2 hours. After cooling, the reaction mixture was partitioned between toluene (100 ml) and dilute hydrochloric acid (400 ml). The aqueous layer was extracted with diethyl ether, cooled in an ice bath then basified with concentrated ammonia and reextracted with dichloromethane. The combined dichloromethane extracts were washed with water, dried and the solvent removed in vacuo. The residue was purified by chromatography on neutral alumina (grade III) eluting with 1% methanol in dichloromethane, followed by trituration with toluene to give 2-(2-imidazolin-2-yl)-1-phenyl-1H-indole as a white solid: yield 16.6 g (90%); mp 180.5°-182° C. The hydrochloride salt was prepared as described above: yield 16.3 g (95%); mp 263.5°-265.5° C.

EXAMPLE 2

2-(2-Imidazolin-2-yl)-1-(2-pyridyl)-1H-indole

A suspension of methyl 1H-indole-2-carboxylate (5.04 g), 2-bromopyridine (3.3 ml), potassium carbonate (7.9 g) and copper (II) oxide (3.9 g) in dry pyridine (80 ml) was heated under reflux for 48 hours. The solvent was removed in vacuo and dichloromethane added to the residue. After filtration the solvent was removed once again in vacuo and the resultant brown oil purified by column chromatography on silica eluting with diethyl ether in petroleum ether (bp 40°-60° C.). Methyl 1-(2-pyridyl)-1H-indole-2-carboxylate was obtained as a white solid: yield 4.74 g (65%). NMR ($CDCl_3$) 3.7 (3H,s,$CH_3$), 7.46 (8H,m,Ar—H), 8.60 (1H,m,Ar—H).

The above ester was converted to 2-(2-imidazolin-2-yl)-1-(2-pyridyl)-1H-indole using the general method given in Example 1(a) using trimethylaluminium and ethylenediamine and was recrystallised from ethyl acetate: yield 30%; mp 158°-159° C.

EXAMPLE 3

2-(2-Imidazolin-2-yl)-1-phenyl-1H-indol-4-ol a) 2-(2-Imidazolin-2-yl)-4-methoxy-1-phenyl-1H-indole.

A solution of 4-methoxy-1H-indole-2-carboxylic acid (16 g; Blaikie K G, Perkin W H, J. Chem. Soc. Trans. 1924, 125, 296) in methanol (400 ml) and concentrated sulphuric acid (16 ml) was heated under reflux for 18 hours. The solvent was removed in vacuo and the residue poured cautiously into sodium carbonate solution. The resultant precipitate was extracted into dichloromethane, the combined organic extracts washed with water, dried and the solvent removed in vacuo. Methyl 4-methoxy-1H-indole-2-carboxylate (15.37 g) was collected as a fawn solid. A portion (7.11 g) of this solid was arylated with bromobenzene using the general method given in Example 2 to give methyl 4-methoxy-1-phenyl-1H-indole-2-carboxylate (6.22 g), 5.01 g of which were converted to 2-(2-imidazolin-2-yl)-4-methoxy-1-phenyl-1H-indole (2.74 g) by treatment with trimethylaluminium and ethylenediamine as described in Example 1(a). A portion of this base was then converted to the hydrochloride salt and recrystallised to give a white solid with a melting point of 247°–248° C.

b) 2-(2-Imidazolin-2-yl)-1-phenyl-1H-indol-4-ol.
Boron tribromide (1.34 ml) was added dropwise to a stirred solution of the hydrochloride salt of 2-(2-imidazolin-2-yl)-4-methoxy-1-phenyl-1H-indole (1.15 g) in dry dichloromethane (100 ml) at −78° C. under argon. The reaction mixture was stirred at room temperature for 3 hours then cooled to −78° C. before quenching with methanol (5.5 ml). The reaction mixture was poured into dilute sodium hydroxide solution, extracted with dichloromethane and the aqueous layer was then acidified with concentrated hydrochloric acid and rebasified with ammonia solution. The yellow precipitate was collected by filtration, washed with water, dried and purified by column chromatography on silica. Elution with 5% methanolic ammonia in dichloromethane gave 2-(2-imidazolin-2-yl)-1-phenyl-1H-indol-4-ol which was converted to its hydrochloride salt using ethereal hydrogen chloride, yield 0.65 g (60%); mp >270° C.

EXAMPLE 4

2-(2-Imidazolin-2-yl)-1-methyl-1H-indole

A stirred suspension of methyl 1H-indole-2-carboxylate (5.0 g), dimethyl sulphate (9 ml) and potassium carbonate (10.4 g) in dry acetone (200 ml) was heated under reflux for 24 h. After cooling to room temperature 5% ammonia solution (50 ml) was added and the mixture stirred for 2 hours. The solvent was removed in vacuo and the residue partitioned between dichloromethane and water. The organic layer was dried and the solvent evaporated to give methyl 1-methyl-1H-indole-2-carboxylate (5.4 g) as a white solid; IR (CHBr$_3$) max 1695 cm$^{-1}$. The ester was treated with ethylenediamine and trimethylaluminium as described in Example 1(a). Purification via column chromatography on silica eluting with 5% v/v methanolic ammonia in dichloromethane gave 2-(2-imidazolin-2-yl)-1-methyl-1H-indole as a white solid. The hydrochloride salt was prepared as in Example 3 and that recrystallised from ethanol/diethyl ether; mp 290°–295° C. (decomp) (Literature mp 260°–280° C. (decomp) D. J. Hlasta, D. Luttinger, M. H. Perrone, M. J. Silbernagel, S. J. Ward and D. R. Haubrich, J. Med. Chem. 1967, 30, 1555).

EXAMPLE 5

2-(2-Imidazolin-2-yl)-1-propyl-1H-indole

A suspension of methyl 1H-indole-2-carboxylate (5.0 g) and sodium hydride (60% dispersion in oil, 1.3 g) in dry dimethylsulphoxide was stirred at 60° C. for 30 minutes. The reaction mixture was cooled to room temperature before adding 1-bromopropane (2.85 ml) and then heated at 60°–80° C. for 3 hours. The cooled reaction mixture was poured into dilute hydrochloric acid and extracted with diethyl ether. The combined organic extracts were washed with water, dried (MgSO$_4$) and the solvent removed in vacuo. The crude product was purified by chromatography on silica, and elution with 10% v/v diethyl ether in petroleum ether (bp 40°–60° C.) gave methyl 1-propyl-1H-indole-2-carboxylate (5.23 g) as a clear oil; NMR (CDCl$_3$) δ0.93 (3H,t,J=7 Hz, C—CH$_3$), 1.82 (2H, sext,J=7 Hz,C—CH$_2$—C), 3.89 (3H,s,OCH$_3$), 4.52 (2H,t,J=7 Hz, N—CH$_2$), 7.15 (4H,m,Ar—H), 7.67 (1H,m,Ar—H). The ester was converted to 2-(2-imidazolin-2-yl)-1-propyl-1H-indole hydrochloride using trimethylaluminium and ethylenediamine as described in Example 1(a); mp 186.5°–187° C.

Table 1 gives further examples of compounds of the invention all having the general structure of formula 1 and prepared by the indicated methods of the above Examples

TABLE 1

| Example | R | R$^1$ | R$^2$ | R$^3$ | n | Method | Melting Point °C. |
|---|---|---|---|---|---|---|---|
| 6 | phenyl | H | methyl | H | 1 | 1 (a) | 167–169$^a$ |
| 7 | phenyl | H | H | methyl | 1 | 1 (a) | 158–160$^a$ |
| 8 | phenyl | H | H | H | 2 | 1 (a) | 218–219$^b$ |
| 9 | phenyl | H | H | H | 3 | 1 (a) | 161–163$^c$ |
| 10 | 3-pyridyl | H | H | H | 1 | 2 | >250$^c$ |
| 11 | 3-hydroxyphenyl | H | H | H | 1 | 3 | 145–165$^d$ |
| 12 | 2-propenyl | H | H | H | 1 | 5 | 210–211$^b$ |
| 13 | cyclopropylmethyl | H | H | H | 1 | 5 | 151–152$^c$ |
| 14 | 2-propenyl | H | H | H | 2 | 5 | 107–108$^c$ |

$^a$tartrate salt
$^b$hydrochloride salt
$^c$free base
$^d$free base (solvated)

Compounds of the invention were screened for their ability to induce insulin secretion using an in vitro test method based on that of Ostenson et al (Am. J. Physiol 1989 257 E439–443).

Islets were isolated from female Wistar rats (body weight 180–300 g) allowed free access to food and water. Islet isolation was performed by a standard collagenase digestion procedure, and individual islets were hand-picked with a finely drawn glass pipette, under a dissecting microscope.

Following initial selection, islets were re-picked into fresh sterile buffer (a physiological saline solution buffered with bicarbonate/CO$_2$ to pH 7.4) and washed three times with 10 ml of this buffer. They were then washed a further twice with 10 ml of sterile buffer supplemented with penicillin (400 IU/ml) and streptomycin (200 μg/ml). Finally, islets were resuspended in 20 ml of tissue culture medium RPMI-1640 containing penicillin and streptomycin, and transferred to sterile culture dishes.

Islets were cultured for 24h at 37° C. under an atmosphere of 5% CO$_2$:95% air at 100% humidity. Following the culture period they were washed in 10 ml of buffered physiological saline solution (pH 7.4) resuspended in a further 10 ml of this solution, and then preincubated at 37° C. for 30 minutes prior to use in experiments.

For each experiment, groups of three individual islets were hand picked into 0.5 ml of buffer containing glucose and the test compound at concentrations of 16.7 mM and 100μM respectively. Test solutions were incubated at 37° C. for 60 minutes and then sampled for assay of insulin by a standard radioimmunoassay procedure.

Results were expressed as percentage increase in insulin secretion above the control which contained 16.7 mm glucose but no test compound.

Table 2 gives the results for a number of the compounds of the invention:

Table 2

% increase in insulin secretion in presence of 16.7 mm glucose and 100μm test compound.

| Example No | % Increase in insulin secretion |
|---|---|
| 1 | 33% |
| 4 | 71% |
| 5 | 40% |
| 10 | 81% |
| 12 | 29% |

The pharmaceutical compositions may be in a form suitable for oral or rectal administration. Such oral compositions may be in the form of capsules, tablets, granules or liquid preparations such as elixirs, syrups or suspension.

Tablets contain a compound of formula 1 or a non-toxic salt thereof in admixture with excipients which are suitable for the manufacture of tablets. These excipients may be inert diluents such as calcium phosphate, microcrystalline cellulose, lactose, sucrose or dextrose; granulating and disintegrating agents such as starch; binding agents such as starch, gelatine, polyvinylpyrrolidone or acacia; and lubricating agents such as magnesium stearate, stearic acid or talc.

Compositions in the form of capsules may contain the compound or a non-toxic salt thereof mixed with an inert solid diluent such as calcium phosphate, lactose or Kaolin in a hard gelatine capsule.

For the purpose of convenience and accuracy of dosing the compositions are advantageously employed in a unit dosage form. For oral administration the unit dosage form contains from 25 to 500 mg, preferably 50 to 250 mg of the compound of formula 1 or a non-toxic salt thereof.

The invention is further illustrated by the following Examples of compositions in which all parts are by weight.

EXAMPLE I

A mixture of one part 2-(2-imidazolin-2-yl)-1-phenyl-1H-indole and four parts microcrystalline cellulose together with 1% of magnesium stearate is compressed into tablets. Conveniently the tablets are of such a size as to contain 25, 50, 100 or 250 mg of the active ingredient.

Example II

A mixture of one part 2-(2-imidazolin-2-yl)-1-phenyl-1H-indole and four parts spray dried lactose together with 1% magnesium stearate is filled into hard gelatine capsules. The capsules may conveniently contain 25, 50, 100 or 250 mg of the active ingredient.

Examples III and IV

The formulations of Examples I and II are varied by replacing the 2-(2-imidazolin-2-yl)-1-phenyl-1H-indole by 2-(2-imidazolin-2-yl)-1-(2-pyridyl)-1H-indole.

Examples V and VI

The formulations of Examples I and II are varied by replacing the 2-(2-imidazolin-2-yl)-1-phenyl-1H-indole by 2-(2-imidazolin-2-yl)-1-(3-pyridyl)-1H-indole.

We claim:

1. A compound of formula I:

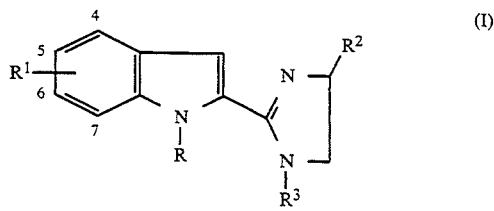

wherein
$R^1$ is hydrogen or hydroxy;
$R^2$ is hydrogen or methyl;
$R^3$ is hydrogen or methyl; and
R is 2-pyridyl, 3-pyridyl or —$C_6H_4$—$R^4$, where $R^4$ is hydrogen or hydroxy, or a non-toxic salt thereof.

2. A compound of formula I according to claim 1, wherein:
$R^1$ is in the 4 position;
$R^2$ and $R^3$ are both hydrogen, or one of $R^2$ and $R^3$ is methyl and the other is hydrogen; and
R is 2-pyridyl, 3-pyridyl or —$C_6H_4$—$R^4$, where $R^4$ is hydrogen or 3-hydroxy, or a non-toxic salt thereof.

3. A compound of formula I according to claim 1 which is 2-(2-imidazolin-2-yl)-1-phenyl-1H-indole.

4. A compound of formula I according to claim 1 which is 2-(2-imidazolin-2-yl)-1-(2-pyridyl)-1H-indole.

5. A compound of formula I according to claim 1 which is 2-(2-imidazolin-2-yl)-1-(3-pyridyl)-1H-indole.

6. A compound of formula I as claimed in claim 1 which is 2-(2-imidazolin-2-yl)-1-phenyl-1H-indol-4-ol.

7. A compound of formula I as claimed in claim 1 which is 2-(4-methyl-2-imidazolin-2-yl)-1-phenyl-1H-indole.

8. A compound of formula I as claimed in claim 1 which is 2-(1-methyl-2-imidazolin-2-yl)-1-phenyl-1H-indole.

9. A compound of formula I as claimed in claim 1 which is 1-(3-hydroxyphenyl)-2-(2-imidazolin-2-yl)-1H-indole.

10. A pharmaceutical composition which comprises a pharmaceutically effective amount of at least one compound according to claim 1 or a non-toxic salt thereof, and a pharmaceutically acceptable carrier or diluent.

11. A pharmaceutical composition according to claim 10 which is in unit dosage form.

12. A pharmaceutical composition according to claim 11 for oral administration wherein each dosage unit contains from 25 to 500 mg of the compound or a non-toxic salt thereof.

13. A pharmaceutical composition according to claim 12 wherein each dosage unit contains from 50 to 250 mg of the compound or a non-toxic salt thereof.

14. A method of treating diabetes which comprises administering to a patient in need thereof an effective amount of a compound of formula I:

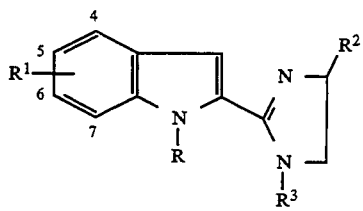 (I)

wherein:

R¹ is hydrogen or hydroxy;

R² is hydrogen or methyl;

R³ is hydrogen or methyl; and

R is 2-pyridyl, 3-pyridyl or —C₆H₄—R⁴, where R⁴ is hydrogen or hydroxy, or a non-toxic salt thereof.

15. A pharmaceutical composition comprising an effective amount of 2-(2-imidazolin-2-yl)-1-phenyl-1H-indole or a non-toxic salt thereof, and a pharmaceutically acceptable carrier or diluent.

16. A method of treating diabetes which comprises administering to a patient in need thereof an effective amount of 2-(2-imidazolin-2-yl)-1-phenyl-1H-indole or a non-toxic salt thereof.

* * * * *